United States Patent [19]

Schumann

[11] Patent Number: Plant 5,930

[45] Date of Patent: Apr. 7, 1987

[54] GERANIUM PLANT NAMED DISCO

[75] Inventor: Ingeborg Schumann, Bad Ems, Fed. Rep. of Germany

[73] Assignee: Fischer Geraniums, Inc., Netherlands Antilles

[21] Appl. No.: 761,010

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Disco having red flower color; semi-double flower form; large flowerhead; good rooting; fast growth; very early flowering response, and excellent flower production.

1 Drawing Figure

The present invention comprises a new and distinct cultivar of geranium, botanically known as *Pelargonium zonale,* and hereinafter referred to by the cultivar name Disco.

Disco is a product of a planned breeding program which had the objective of creating new geranium cultivars having red flower color, semi-double flower form, good rooting, fast growth, and very early flowering response.

Disco was originated from a hybridization made by Ingeborg Schumann in a controlled breeding program in Hillscheid, Federal Republic of Germany in 1980. The female parent was an inbred line of Purlapen. The male parent of Disco was an inbred line of Dresden Doll. Both parents are unpatented.

Disco was discovered and selected as one flowering plant within the progeny of the stated cross by Ingeborg Schumann in June of 1981 in a controlled environment in Hillscheid, Federal Republic of Germany.

The first act of asexual reproduction of Disco was accomplished when vegetative cuttings were taken from the initial selection in January of 1982 in a controlled environment in Hillscheid, Federal Republic of Germany by a technician working under formulations established and supervised by Ingeborg Schumann. Horticultural examination of selected units initiated in the spring of 1982 and continuing in 1983 and 1984 has demonstrated that the combination of characteristics as herein disclosed for Disco are firmly fixed and are retained through successive generations of asexual reproduction.

Disco has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Disco, which in combination distinguish this geranium as a new and distinct cultivar.

1. Red flower color with a dark eye; there is purple tinging in petals.
2. Semi-double flower form.
3. Good rooting.
4. Fast growth.

5. Large umbel or flowerhead positioned above compact foliage.
6. Medium green foliage.
7. Very early flowering response and excellent flower production.
8. Good chlorophyll quality for transportation.

Of the many commercial cultivars known to the present inventor, the most similar in comparison to Disco are Purlapen and Polka, the latter being disclosed in U.S. Plant Pat. No. 5,371. Reference is made to the attached Chart A which compares certain characteristics of Disco to those same characteristics of Purlapen and Polka. In comparison to Purlapen, Disco has a more intensive red color with a dark eye, no blueing in old flowers, earlier flowering response, and a larger flowerhead. The flower color of Disco is also more intense than Polke, which is RHS 46C.

The accompanying photographic drawings shows typical flower and foliage characteristics of Disco, with colors being as true as possible with illustrations of this type.

In the following description color references are made to The Royal Horticultural Society Colour Chart. The color values were determined between 4:00 p.m. and 5:00 p.m. on May 21, 1985 under 15,000 Lux light intensity at Hillscheid, Federal Republic of Germany.

Classification:

*Botanical.*—A hybrid of the genus *Pelargonium l'hert* and species *Pelargonium zonale.*

*Commercial.*—Disco.

INFLORESCENCE

A. Umbel:

*Average diameter.*—122 mm.

*Average depth.*—80 mm.

*Peduncle length.*—240 mm.

*Pedicel length.*—24 mm.

B. Corolla:

*Average diameter.*—47 mm.

*Form.*—Semi-double.

*Color (general tonality from a distance of three meters).*—Red. Upper Surface: 45B with a dark eye, and purple tinging.

C. Bud:

*Shape.*—Round to oval.

*Color.*—Red-purple; marbled.

D. Reproductive organs:

*Androecium.*—4–10 stamens.

*Gynoecium.*—5–6 lobed stigma.

E. Spring flowering response period: In Hillscheid, Federal Republic of Germany, in 1982, 80% of plants opened with at least one flower 13 weeks after planting of unrooted cuttings.

F. Outdoor flower production: The total flower count in 1982 in Hillscheid, Federal Republic of Germany, was between 45 and 50 flowers per plant for the June through October observation period.

G. Durability: Shatter resistance good.

PLANT

A. Foliage:

*Form.*—Kidney shaped.

*Margin.*—Generally round, crenate.

*Color.*—Top surface: Medium green, approximately 137B-C. Zonation: Very slight zonation.

*Tolerance of botrytis.*—Good.

B. General appearance and form:

*Internode length.*—25 mm.

*Branching pattern.*—3.5 branches per plant.

*Height.*—280 mm.

CHART A

| CULTIVAR | EARLY FLOWER RESPONSE (% of plants in flower after 13 weeks) | UMBEL SIZE |
|---|---|---|
| Disco | 80% | 122 mm |
| Purlapen | 70% | 101 mm |
| Polka | 75% | 119 mm |

| CULTIVAR | ZONATION | MARKS |
|---|---|---|
| Disco | Little | Dark eye in corolla |
| Purlapen | None | None |
| Polka | Middle | None |

I claim:

1. A new and distinct cultivar of geranium named Disco, as described and illustrated, and particularly characterized by its red flower color; semi-double flower form; large flowerhead; good rooting; fast growth; very early flowering response, and excellent flower production.

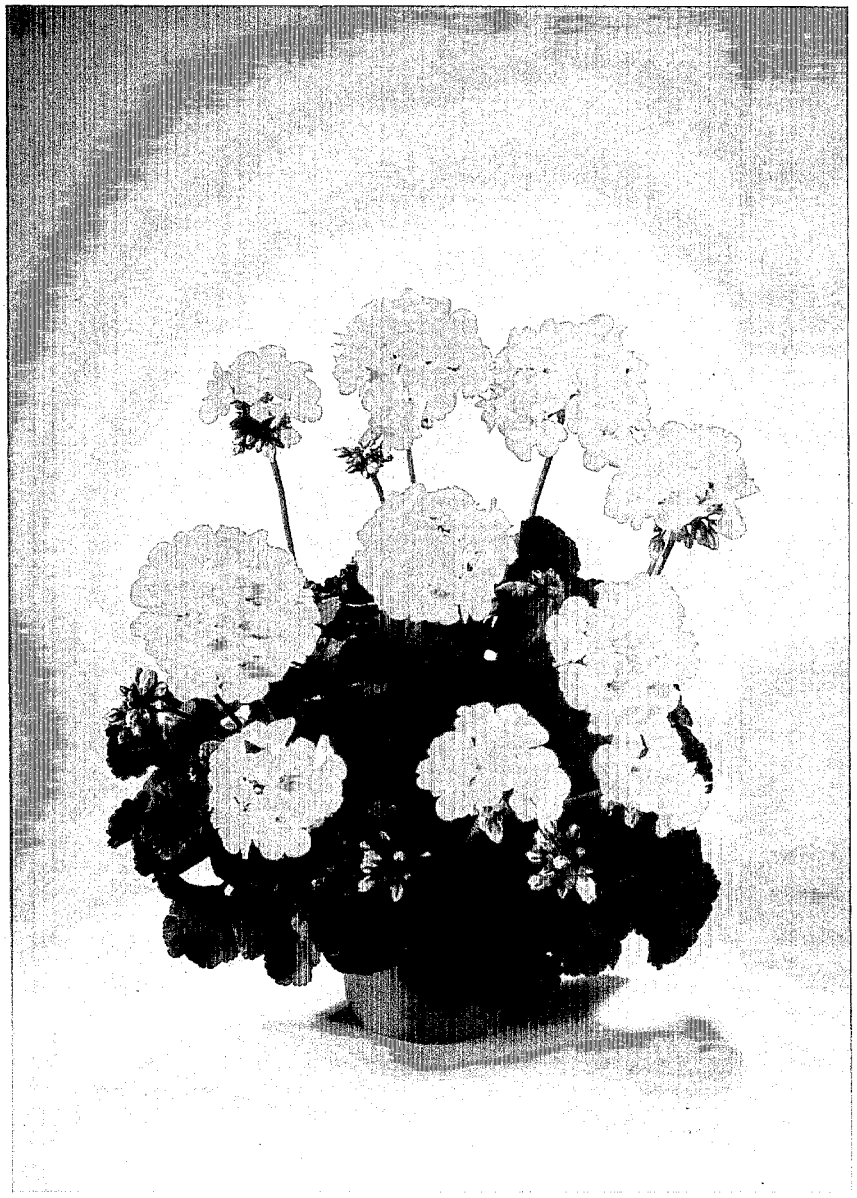

* * * * *